United States Patent [19]

Akerkar et al.

[11] 4,276,280

[45] Jun. 30, 1981

[54] RADIOLABELED DERIVATIVES OF FOLIC ACID

[75] Inventors: Anandrao S. Akerkar, Pomona, N.Y.; Herman Rutner, Hackensack, N.J.

[73] Assignee: Becton, Dickinson and Company, Paramus, N.J.

[21] Appl. No.: 727,408

[22] Filed: Sep. 29, 1976

[51] Int. Cl.$^3$ .................... A61K 43/00; C07D 475/04; G01T 1/16
[52] U.S. Cl. .................................... 424/1; 23/230 B; 260/112.5 R; 544/258
[58] Field of Search ..................... 260/251.5, 112.5 R; 424/1; 23/230 B

[56] References Cited

U.S. PATENT DOCUMENTS

| | | | |
|---|---|---|---|
| 3,988,431 | 10/1976 | Givas et al. | 424/1.5 |
| 3,989,812 | 11/1976 | Barrett et al. | 424/1 |

*Primary Examiner*—Paul M. Coughlan, Jr.
*Attorney, Agent, or Firm*—Louis E. Marn; Elliot M. Olstein

[57] ABSTRACT

Derivatives of folic acid wherein the α-carboxyl group of the glutamyl moiety is substituted with a radical which is capable of being radioiodinated, such as, substituted and unsubstituted tyrosyl and histidyl. The radioiodinated derivatives can be employed as tracers for the assay of folates.

32 Claims, No Drawings

RADIOLABELED DERIVATIVES OF FOLIC ACID

This invention relates to derivatives of folic acid (pteroyl glutamic acid), and more particularly, to radiolabeled derivatives of folic acid, intermediates for the preparation of such radiolabeled derivatives; the assay of folates with such derivatives, and the method of preparing such folates.

Folate (folic acid) deficiency is present in about one-third of all the pregnant women in the world, the vast majority of alcoholics, the majority of people who eat a diet of fresh uncooked fruits, or fresh uncooked vegetables or fresh fruit juices, many people with structural or functional damage in the upper third of the small bowel (including patients with tropical or nontropical sprue or a wide variety of malabsorption syndromes) and in number of other situations. Measurement of both serum and red cell folate levels constitutes the most direct and reliable means of determining the existence of folate deficiency, and these tests should be performed for every patient who has a megaloblastic anemia, as well as every patient who has anemia, hypersegmentation of granulocyte nuclei, and coincident evidence of iron deficiency.

The finding of low serum folate means that the patients recent diet has been subnormal in folate content and/or that his recent absorbability of folate has been subnormal, but does not prove that patient has or will develop tissue folate depletion requiring folate therapy. A low red cell folate can mean either that there is tissue folate depletion due to folate deficiency requiring folate therapy, or alternatively, that the patient has primary Vitamin $B_{12}$ deficiency blocking the availability of cells to take up folate, in which case the proper therapy would be with Vitamin $B_{12}$ rather than with folic acid. It is for these reasons that it is advisable to determine red cell folate in addition to serum folate, and thereby definitely determine that the diagnosis is folate deficiency for which the proper treatment is folic acid.

Endogenous folate is measured by a competitive binding technique which involves the ability of unlabeled folate in serum or other media to compete with labeled folic acid for a specific folate binder, present in usable concentrates, in such sources as cows milk, hog kidney, etc., and thereby inhibit the binding of labeled folic acid. As a result of the competitive inhibition, the ratio of bound labeled folic acid to free labeled folic acid diminishes as the concentration of unlabeled folate is increased. Accordingly, the concentration of folate in an unknown sample; e.g., a patient's blood, is obtained by comparing the inhibition observed with that produced by known amounts of folate, as presented in a standard curve. The labeled folic acid generally employed in the assay is a radiolabeled folic acid, such as folic acid radiolabeled with tritium, and there is a need for improved radiolabeled compounds for the assay of folates by a radioassay technique.

An object of the present invention is to provide derivatives of folic acid which can be employed for the assay of folates.

Another object of the present invention is to provide radiolabeled derivatives of folic acid and intermediates for the preparation thereof.

A further object of the present invention is to provide for an improved radioassay for folates.

These and other objects of the present invention should be more apparent from reading the following description thereof.

In accordance with the present invention there is provided derivatives of folic acid wherein the α-carboxyl group is substituted with an amino compound having an aromatic or heterocyclic ring substituent which is capable of being radiolabeled.

More particularly, in accordance with the present invention, there is provided novel derivatives of folic acid having the following structural formula:

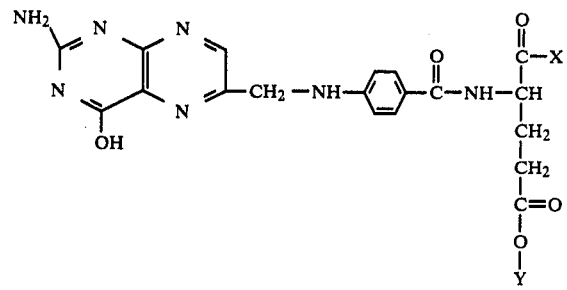

wherein Y is—H or an alkali metal, ammonia or amine salt thereof; lower alkyl (1-6 carbon atoms, preferably methyl or ethyl); X is an unlabeled or radiolabeled amine or amino acid derivative including a phenolic, aromatic or heterocyclic ring capable of being radiolabeled, preferably one of the following:

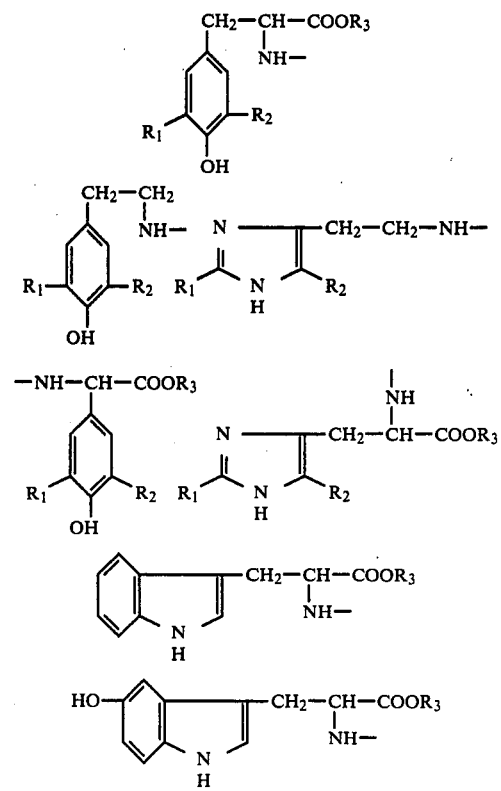

Wherein $R_1$ and $R_2$ are each separately hydrogen, fluoro, chloro, bromo, nitro, lower (1-6 carbon atoms) alkoxy, lower (1-6 carbon atoms) alkyl, or a radioactive isotope of iodine wherein at least one of $R_1$ and $R_2$ is hydrogen when the radical is unlabeled and at least one of $R_1$ and $R_2$ is a radioactive isotope of iodine when the radical is radiolabeled, and $R_3$ is hydrogen, lower alkyl (1-6 carbon atoms, preferably methyl or ethyl), an alkali metal, an alkaline earth metal or amine.

The radioactive isotope of iodine is preferably $I^{125}$, $I^{131}$ or $I^{123}$.

The preferred radiolabeled compounds are the radioiodinated derivatives in which Y and $R_3$ are —H in that such derivatives are similar to folic acid with respect to lipophilicity, polarity, solubility and hydrophilicity, with the substituted and unsubstituted tyrosyl and histidyl derivatives being particularly preferred. Such preferred compounds are generally mono-radioiodinated.

In the above compounds, in the case where X has optically active isomers, X may be in the L-, D-, or DL-form, with the L-form being most preferred.

The compounds of the present invention are prepared by condensation of folic acid with the appropriate amine or amino acid derivative with a suitable condensing agent in a solvent system, followed by separation of the α-substituted derivative. The radioiodinated compounds can be prepared by radioiodination of the α-substituted derivative by one of the conventional procedures known in the art.

More particularly, folic acid is condensed with the appropriate amine or amino acid derivative; e.g., tyrosine or a substituted tyrosine in the presence of a condensing agent conventionally employed for the production of peptides. As representative examples of such agents, there may be mentioned: 1-ethyl-3-(3-dimethylaminopropyl) carbodiimide or its hydrochloride salt; dicyclohexyl carbodiimide; 1-ethyl-3-(4-morpholinyl) carbodiimide or its HCl salt; 1-isopropyl-3-(3-dimethylaminopropyl) carbodiimide or its HCL salt; 1-cyclohexyl-3-(3-dimethylaminopropyl) carbodiimide or its HCl salt. The present invention is not limited to such condensing agents, and the selection of a suitable condensing agent is deemed to be within the scope of those skilled in the art from the teachings herein.

The condensation is effected in a suitable solvent for the folic acid and appropriate derivative. The preferred solvent system is a mixture of water and a water miscible organic solvent, such as pyridine, dioxane, tetrahydrofuran, dimethylformamide, dimethylsulfoxide, dimethylacetamide, and the like. The preferred system is pyridine and water. In some cases, it is possible to employ a mixture of water and a non-water miscible organic solvent, in combination with a suitable base, such as, pyridine, triethylamine, N-methylmorpholine, etc. The selection of a suitable solvent system is deemed to be within the scope of those skilled in the art from the teachings herein.

The condensation is generally effected at a temperature of from about 0° to 65° C., preferably from about 5° to 30° C. The pH of the reaction is generally from about 5 to 10, preferably from about 7-9.

The reaction mixture contains unreacted folic acid, disubstituted folic acid, α-substituted folic acid and γ-substituted folic acid. In accordance with the present invention, the disubstituted derivative is selectively removed from an aqueous solution of the mixture by appropriate adjustment of the pH, generally a pH of from 8-12, preferably 8.5 to 10.

After separating the disubstituted derivative, the desired α-substituted product is selectively precipitated from the mixture by appropriate adjustment of the pH, generally a pH of from about 2-5, preferably 2.5-3.

The separated α-substituted derivative can then be radioiodinated by conventional procedures to produce the radioiodinated derivatives of the present invention. Alternatively, the appropriate amine or amino acid derivative can be radioiodinated prior to the condensation with the folic acid, in which case, radioiodination subsequent to the condensation is not necessary.

In accordance with a preferred aspect of the present invention, the preferred intermediates for preparing the radioiodinated derivatives are those in which one of $R_1$ and $R_2$ is hydrogen and one of $R_1$ and $R_2$ is fluoro, chloro, bromo, nitro, lower alkyl or lower alkoxy in that subsequent radioiodination produces a monoradioiodinated derivative. Alternatively, as a preferred procedure, the derivative to be condensed with folic acid is an amine or amino acid derivative in which one of $R_1$ and $R_2$ is a radioactive isotope of iodine and one of $R_1$ and $R_2$ is fluoro, bromo, chloro, lower alkoxy, lower alkyl or nitro.

As an alternative procedure for preparing the compounds of the present invention, folic acid is converted to the anhydride in the presence of a suitable condensing agent, such as dicyclohexyl carbodiimide, followed by condensation of the anhydride with the appropriate amine or amino acid derivative.

The invention will be further described with respect to the following examples; however, the scope of the invention is not to be limited thereby.

EXAMPLE I

A. A mixture of 230 mg of L-tyrosine methyl ester hydrochloride, 440 mg of pteroyl glutamic acid and 250 mg of 1-ethyl-3-(3-dimethylaminopropyl) carbodiimide hydrochloride was dissolved in 10 ml of 1:1 pyridine water and stirred at room temperature for one hour and 4° C. for 16 hours. The reaction mixture was diluted with 10 ml 0.5% sodium bicarbonate solution and filtered. The filtrate was acidified to pH 2.5 using 0.5 N HCl solution. The solid α-(pteroyl glutamyl)-L-tyrosine methyl ester was filtered, washed with cold water and dried in vacuo. M.P. 255°-56° (decomposition) Log $\epsilon$ 4.44 and 283 nm (0.1 N NaOH) $R_f$ 0.46 (paper chromatography, 0.5% NaHCO$_3$).

B. A mixture of 243 mg of DL-3-fluoro-tyrosine methy ester hydrochloride, 443 mg of pteroyl glutamic acid and 255 mg of 1-ethyl-3-(3-dimethylamino propyl) carbodiimide hydrochloride was stirred at 0° C. for 2 hours and then 6 hours at room temperature. The reaction mixture was diluted with 15 ml. of 0.4% sodium bicarbonate solution and was filtered. The solid was discarded. The filtrate was acidified and the separated solid α-(pteroylglutamyl)-DL-3-fluoro-tyrosine methyl ester was filtered, washed with 50 ml cold water and dried in vacuo. M.P.>300° C. Log $\epsilon$ 4.44 at 282 nm (0.1 N NaOH) $R_f$ 0.46 (paper chromatography, 0.5% NaHCO$_3$).

The procedure of example IB was also repeated with DL-3-fluorotyrosine ethyl ester, tyramine, histidine methyl ester and histamine to produce the corresponding derivatives of folic acid.

EXAMPLE II

A. Nitrogen gas was bubbled through a mixture of 300 mg of α-(pteroylglutamyl)-L-tyrosine methyl ester and 3 ml of 0.2 N sodium hydroxide solution. After a few minutes the solution was filtered and acidified with 1 N hydrochloric acid. The separated solid α-(pteroylglutamyl)-L-tyrosine was filtered, washed with cold water and dried under vacuum. M.P. 275°-285° (decomposition). U.V. Log ε 4.43 at 283 nm. R_f 0.58 (paper chromatography, 0.5% NaHCO₃).

B. Three milliliters of 0.2 N sodium hydroxide was added to 312 mg of α-(pteroylglutamyl)-D-L-(3-fluoro tyrosine methyl ester) in the presence of nitrogen gas. The mixture was quickly acidified and diluted with 10 ml cold water. The solid α-(pteroylglutamyl)-DL-3-fluoro-tyrosine was filtered and dried. M.P. >300° C. U.V. Log ε 4.42 at 282 nm R_f 0.59 (paper chromatography using 0.5% NaHCO₃).

The procedure is repeated with α-(pteroylglutamyl)-L-histidine methyl ester to produce the corresponding histidyl derivative of folic acid.

EXAMPLE III

A. Iodination of 60 μg α-(pteroylglutamyl)-L-tyrosine produced by the procedure of Example IIA with 10 mC $^{125}$I is effected at pH 7.4 by the method of Hunter and Greenwood at a substrate to iodine ratio of 20 to 1. Unreacted iodine is removed by passage through a quaternaryamine anion exchange resin in the chloride form. The co-absorbed product is eluted and contains 8.5 mC in the two iodination products, α-(pteroylglutamyl)-3-iodo-tyrosine and α-(pteroylglutamyl)-3,5-diiodotyrosine which are formed in the ratio of 7 to 1. Also formed are some fragments of folic acid. The separation of the mono and diiodinated products was achieved by cellulose column chromatography.

This procedure is repeated with α-(pteroylglutamyl)-L-tyrosine. The ratio of mono and diiodinated products obtained is 8 to 1.

B. Iodination of 21.5 μg α-(pteroylglutamyl)-DL-3-fluoro-tyrosine produced by the procedure of Example IIB with 5 mC $^{125}$I is effected at pH 7.4 by the method of Hunter and Greenwood at a substrate to iodine ratio of 20 to 1. Unreacted iodine is removed by passage through a quaternary amine anion exchange resin in the chloride form. The co-absorbed form is eluted with a mixture of tetrahydrofuran and hydrochloric acid and contains 4.3 mC in the monoiodination product α-(pteroylglutamyl)-DL-3-fluoro-5-iodo-tyrosine. The pure product is separated from the fragments by passage through a cellulose column.

This procedure is repeated with α-(pteroylglutamyl)-L-histamine and α-(pteroylglutamyl)-L-histidine as produced by the procedure in Example IIB.

The radioiodinated derivatives of the present invention may be used as the labeled antigen in the radioassay of folic acid. A radioassay procedure which may be employed is one which is disclosed by Givas et al.; Clin. Chem., Vol. 21, pp 427-428 (March 1975) for tritium labeled folic acid as follows:

To 50 microliter of serum in disposable glass tube in 1.5 ml Lysine buffer (pH 9.2±0.2) is added, with thorough mixing the calculated amount of radioiodinated derivative of the present invention. Folate binding protein is then added in sufficient amount to produce 50%±10% binding of the radioiodinated derivative in the absence of unlabeled drug, and the mixture is incubated at 25° C. for 30 minutes. Competition between the radioiodinated compound and unlabeled 5-methyl tetrahydrofolic acid for protein binding sites determines the amount of radioiodinated compound-antibody complex present at equilibrium. Separation of bound from free radioiodinated compound is achieved by the dextran coated charcoal technique, resulting in selective binding of the free labeled and unlabeled compound to the coated charcoal, which is then separated by centrifugation. The separation phase is decanted and counted in a gamma counter.

The radioiodinated folic acid derivatives of the present invention are an improvement over the tritiated folic acid presently employed in the art for the radioassay of folic acid for the following reasons:

1. An inexpensive well counter may be used as compared to the costly and complex liquid scintillation counter required for the tritiated compounds.

2. Liquid scintillation fluids and special vials are not needed.

3. No internal or external standardizations are needed as in the case of tritiated folic acid.

4. Counting efficiencies are higher, particularly in aqueous media.

More specifically, radioiodinated folic acid derivatives can be made at higher specific activity than tritiated folic acid. The relatively low specific activity and the lower counting efficiency of tritiated folic acid limit its commercial value.

In addition, the radioiodinated derivatives, of the present invention in which the amino acid moiety is in the acid form, instead of the ester form, significantly increases the polarity, solubility and hydrophilicity of the compound whereby such derivatives are water soluble at physiological pH values; can be iodinated in aqueous media; possesses a side chain more nearly comparable in polarity to folic acid, exhibit superior binding to the binding protein, and shows lesser tendency toward absorption on glass surface or lipophilic surfaces such as plastic test tubes.

Numerous modifications and variations of the present invention are possible in light of the above teachings and, accordingly, within the scope of the appended claims, the invention may be practiced otherwise than as particularly described.

We claim:

1. A compound having the following structural formula:

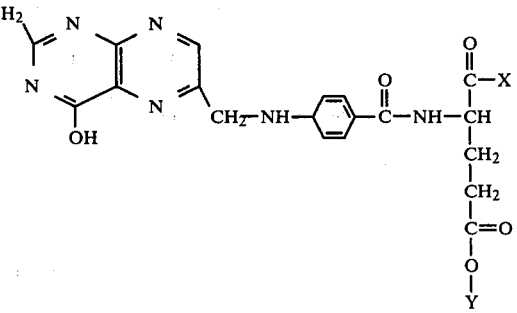

wherein Y is selected from the group consisting of —H, lower alkyl, or a cation selected from the group consisting of alkali metals, alkaline earth metals, and ammonium; X is selected from the group consisting of radicals having the following structural formula:

(a) [structure: CH2-CH-COOR3 with NH-, attached to benzene ring with R1, R2, OH]

(b) [structure: CH2-CH2-NH-, attached to benzene ring with R1, R2, OH]

(c) [imidazole-like structure with CH2-CH2-NH-, R1, R2]

(d) [structure: NH-CH-COOR3, benzene ring with R1, R2, OH]

(e) [imidazole structure with CH2-CH-COOR3, NH, R1, R2]

wherein R₁ and R₂ are each separately selected from the group consisting of hydrogen, fluoro, chloro, bromo-, nitro, lower alkoxy, lower alkyl and radioactive isotopes of iodine, wherein at least one of R₁ and R₂ is a radioactive isotope of iodine, and R₃ is selected from the group consisting of hydrogen, lower alkyl, an alkali metal and an alkaline earth metal.

2. The compound of claim 1 wherein X has structural formula (a).

3. The compound of claim 2 wherein R₃ is hydrogen and Y is —H.

4. The compound of claim 3 wherein R₁ is a radioactive isotope of iodine and R₂ is fluoro.

5. The compound of claim 1 wherein Y is —H, R₃ is hydrogen.

6. The compound of claim 1 wherein X has structural formula (b).

7. The compound of claim 6 wherein Y is —H and R₃ is hydrogen.

8. The compound of claim 1 wherein X has structural formula (c).

9. The compound of claim 8 wherein Y is —H and R₃ is hydrogen.

10. The compound of claim 1 wherein X has structural formula (e).

11. The compound of claim 10 wherein Y is —H and R₃ is hydrogen.

12. The compound of claim 2 wherein R₃ is methyl and Y is —H.

13. A process for producing a compound as defined in claim 1, comprising:
condensing in solution folic acid with a member selected from the group consisting of the amine and amino acid derivatives defined as X in claim 23; adjusting the pH of the solution from about 8-12 to precipitate and separate the di-substituted derivatives; and thereafter adjusting the pH to from about 2-5 to precipitate and separate an α-mono-substituted derivative of folic acid as defined by claim 1.

14. The process of claim 13 wherein the condensation is effected with a peptide condensing agent at a pH of from 5-10.

15. The process of claim 13 wherein X has structural formula (a).

16. The process of claim 15 wherein R₂ is hydrogen.

17. In the radioassay of folates, the improvement comprising:
employing a compound as defined in claim 1 as the tracer.

18. In the radioassay of folates, the improvement comprising:
employing a compound as defined in claim 2 as the tracer in said assay.

19. In the radioassay of folates, the improvement comprising:
employing a compound as defined in claim 3 as the tracer in said assay.

20. In the radioassay of folates, the improvement comprising:
employing a compound as defined in claim 4 as the tracer in said assay.

21. In the radioassay of folates, the improvement comprising:
employing a compound as defined in claim 6 as the tracer in said assay.

22. A compound having the following structural formula:

[structure: pteridine ring with NH2, OH, CH2-NH-phenyl-C(=O)-NH-CH(C(=O)-X)-CH2-CH2-C(=O)-O-Y]

wherein y is selected from the group consisting of —H, lower alkyl, or a cation selected from the group consisting of alkali metals, alkaline earth metals and ammonium; X is selected from the group consisting of radicals having the following structural formula:

(a) [structure: CH2-CH-COOR3 with NH-, benzene ring with R1, R2, OH]

(b) [structure: CH2-CH2-NH-, benzene ring with R1, R2, OH]

(c) [imidazole structure with CH2-CH2-NH-, R1, R2]

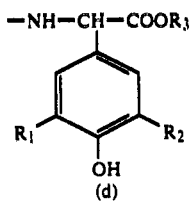
(d)

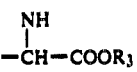
(e)

wherein $R_1$ and $R_2$ are each separately selected from the group consisting of hydrogen, fluoro, chloro, bromo-, nitro, lower alkoxy and lower alkyl, wherein at least one of $R_1$ and $R_2$ is hydrogen, and $R_3$ is selected from the group consisting of hydrogen, lower alkyl, an alkali metal and an alkaline earth metal.

23. The compound of claim 22 wherein X has structural formula (a).

24. The compound of claim 23 wherein one of $R_1$ and $R_2$ is fluoro.

25. The compound of claim 22 wherein X has structural formula (b).

26. The compound of claim 22 wherein X has structural formula (c).

27. The compound of claim 22 wherein X has structural formula (e).

28. A process for producing a compound as defined in claim 22 comprising:
condensing in solution folic acid with a member selected from the group consisting of the amine and amino acid derivatives defined as X in claim 22; adjusting the pH of the solution to from about 8–12 to precipitate and separate the di-substituted derivatives; and thereafter adjusting the pH to from about 2–5 to precipitate and separate an α-mono-substituted derivative of folic acid as defined by claim 22.

29. The process of claim 28 wherein the condensation is effected with a peptide condensing agent at a pH of from 5–10.

30. The process of claim 29 wherein X has structural formula (a), and $R_1$ and $R_2$ are both hydrogen.

31. The compound of claim 22 wherein X has structural formula (d).

32. The compound of claim 1 wherein X has structural formula (d).